US009415100B2

(12) United States Patent
Kim et al.

(10) Patent No.: US 9,415,100 B2
(45) Date of Patent: Aug. 16, 2016

(54) EPITOPE AND ITS USE OF HEPATITIS B VIRUS SURFACE ANTIGEN

(75) Inventors: Se-Ho Kim, Yongin-si (KR);
Kwang-Won Hong, Yongin-si (KR);
Yong-Won Shin, Yongin-si (KR); Ki Hwan Chang, Yongin-si (KR); Min-Soo Kim, Yongin-si (KR); Jung-Ae Im, Yongin-si (KR)

(73) Assignee: GREEN CROSS CORPORATION, Yongin-si (KR)

( * ) Notice: Subject to any disclaimer, the term of this patent is extended or adjusted under 35 U.S.C. 154(b) by 0 days.

(21) Appl. No.: 14/127,052

(22) PCT Filed: Jul. 25, 2011

(86) PCT No.: PCT/KR2011/005477
§ 371 (c)(1),
(2), (4) Date: Dec. 17, 2013

(87) PCT Pub. No.: WO2013/002449
PCT Pub. Date: Jan. 3, 2013

(65) Prior Publication Data
US 2014/0112923 A1 Apr. 24, 2014

(30) Foreign Application Priority Data

Jun. 30, 2011 (KR) ........................ 10-2011-0064671

(51) Int. Cl.
| | | |
|---|---|---|
| *A61K 39/29* | (2006.01) | |
| *C07K 16/08* | (2006.01) | |
| *A01K 67/027* | (2006.01) | |
| *C07K 14/005* | (2006.01) | |
| *A61K 39/00* | (2006.01) | |

(52) U.S. Cl.
CPC ............ *A61K 39/292* (2013.01); *A01K 67/027* (2013.01); *C07K 14/005* (2013.01); *C07K 16/082* (2013.01); *A01K 2207/05* (2013.01); *A01K 2227/105* (2013.01); *A01K 2267/0337* (2013.01); *A61K 2039/53* (2013.01); *C07K 2317/34* (2013.01); *C07K 2317/76* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS

2008/0171062 A1 * 7/2008 Sala-Schaeffer et al. .. 424/204.1

FOREIGN PATENT DOCUMENTS

| KR | 1999008648 A | 2/1999 |
|---|---|---|
| WO | 0012547 A2 | 3/2000 |
| WO | 0028009 A1 | 5/2000 |
| WO | 2004108753 A1 | 12/2004 |
| WO | 2004113370 A1 | 12/2004 |
| WO | 2011078456 | 6/2011 |

OTHER PUBLICATIONS

AAF15849, 1999.*
European Patent Office, Communication dated Jan. 30, 2015, issued in corresponding European Application No. 11868565.0.
Hayashi et al., "Studies on Peptides. CLXVI. Solid-Phase Syntheses and Immunological Properties of Fragment Peptides Related to Human Hepatitis B Virus Surface Antigen(HBsAg) and Its Pre-S2 Gene"; Chem. Pharm. Bull; vol. 36, No. 12; Jan. 1, 1988; pp. 4993-4999; XP55163740.
State Intellectual Property Office of the People's Republic of China, Communication dated Nov. 4, 2014, issued in counterpart Chinese Application No. 201180071967.3.
Accession No. AAF15849, GenBank database.
Accession No. AAF15606, GenBank database.
Honorati et al., Gastroenterology, 1997, vol. 112, No. 6, pp. 2017-2027.
Malaysian Intellectual Property Office; Communication dated Jun. 30, 2015, in counterpart Application No. PI2013004628, Only English Abstract Considered.
Szomor et al., "Mutation spectra of the surface-protein-coding region of the HBV genome in HBV-vaccinated and non-vaccinated individuals in Hungary" Archives of Virology, vol. 153, pp. 1885-1892 (Sep. 24, 2008).

* cited by examiner

*Primary Examiner* — Agnieszka Boesen
(74) *Attorney, Agent, or Firm* — Sughrue Mion, PLLC

(57) ABSTRACT

Disclosed are an epitope specific to hepatitis B virus (HBV) and use thereof. The disclosed epitope is a conservative position on which mutagenesis does not occur and, therefore, a composition including an antibody to the foregoing epitope or a vaccine composition including the epitope has very low possibility of causing degradation of curing efficacy due to HBV mutation, thus being very useful for HBV treatment.

13 Claims, 4 Drawing Sheets

```
                         SEQUENCE LISTING

<160> NUMBER OF SEQ ID NOS: 7

<210> SEQ ID NO 1
<211> LENGTH: 226
<212> TYPE: PRT
<213> ORGANISM: Unknown
<220> FEATURE:
<223> OTHER INFORMATION: HBsAg's subtype adr

<400> SEQUENCE: 1

Met Glu Asn Thr Thr Ser Gly Phe Leu Gly Pro Leu Leu Gly Leu Gln
 1               5                  10                  15

Ala Gly Phe Phe Leu Leu Thr Arg Ile Leu Thr Ile Pro Gln Ser Leu
             20                  25                  30

Asp Leu Trp Trp Thr Ser Leu Asn Phe Leu Gly Gly Ala Pro Lys Cys
         35                  40                  45

Pro Gly Leu Asn Ser Gln Ser Pro Thr Ser Asn His Ser Pro Thr Ser
     50                  55                  60

Cys Pro Pro Ile Cys Pro Gly Tyr Arg Ser Met Cys Leu Arg Arg Phe
 65                  70                  75                  80

Ile Ile Phe Leu Phe Ile Leu Leu Leu Cys Leu Ile Phe Leu Leu Val
                 85                  90                  95

Leu Leu Asp Tyr Gln Gly Met Leu Pro Val Cys Pro Leu Leu Pro Gly
            100                 105                 110

Thr Pro Thr Thr Ser Thr Gly Pro Cys Lys Thr Cys Thr Ser Pro Ala
        115                 120                 125

Gln Gly Asn Ser Thr Phe Pro Ser Cys Cys Cys Thr Lys Pro Ser Asp
    130                 135                 140

Gly Asn Cys Ile Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Ile Val Trp Leu
            180                 185                 190

Ser Val Ile Trp Met Met Trp Tyr Trp Gly Arg Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 2
<211> LENGTH: 226
<212> TYPE: PRT
<213> ORGANISM: Unknown
<220> FEATURE:
<223> OTHER INFORMATION: HBsAg's subtype ayw

<400> SEQUENCE: 2

Met Glu Asn Ile Thr Ser Gly Phe Leu Gly Pro Leu Leu Val Leu Gln
 1               5                  10                  15

Ala Gly Phe Phe Leu Leu Thr Arg Ile Leu Thr Ile Pro Gln Ser Leu
             20                  25                  30
```

```
Asp Ser Trp Trp Thr Ser Leu Asn Phe Leu Gly Gly Thr Val Cys
        35                  40                  45

Leu Gly Gln Asn Ser Gln Ser Pro Thr Ser Asn His Ser Pro Thr Ser
 50                  55                  60

Cys Pro Pro Thr Cys Pro Gly Tyr Arg Trp Met Cys Leu Arg Arg Phe
 65                  70                  75                  80

Ile Ile Phe Leu Phe Ile Leu Leu Cys Leu Ile Phe Leu Leu Val
                 85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Thr Thr Pro Ala
                115                 120                 125

Gln Gly Thr Ser Met Tyr Pro Ser Cys Cys Cys Thr Lys Pro Ser Asp
130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Ser Ile
                195                 200                 205

Leu Ser Pro Phe Leu Pro Leu Leu Pro Ile Phe Phe Cys Leu Trp Val
                210                 215                 220

Tyr Ile
225

<210> SEQ ID NO 3
<211> LENGTH: 832
<212> TYPE: PRT
<213> ORGANISM: Unknown
<220> FEATURE:
<223> OTHER INFORMATION: HBV polymerase protein

<400> SEQUENCE: 3

Leu Leu Leu Asp Asp Glu Ala Gly Pro Leu Glu Glu Glu Leu Pro Arg
 1               5                  10                  15

Leu Ala Asp Glu Gly Leu Asn Arg Arg Val Ala Glu Asp Pro Asn Leu
                20                  25                  30

Gly Asn Leu Asn Val Ser Ile Pro Trp Thr His Lys Val Gly Asn Phe
                35                  40                  45

Thr Gly Leu Tyr Ser Ser Thr Val Pro Val Phe Asn Pro Glu Trp Gln
 50                  55                  60

Thr Pro Ser Phe Pro His Ile His Leu Gln Glu Asp Ile Ile Asn Arg
 65                  70                  75                  80

Cys Gln Gln Tyr Val Gly Pro Leu Thr Ile Asn Glu Lys Arg Arg Leu
                 85                  90                  95

Lys Leu Ile Met Pro Ala Arg Phe Tyr Pro Asn Leu Thr Lys Tyr Leu
                100                 105                 110

Pro Leu Asp Lys Gly Ile Lys Pro Tyr Tyr Pro Glu His Ala Ala Asn
                115                 120                 125

His Tyr Phe Lys Thr Arg His Tyr Leu His Thr Leu Trp Lys Ala Gly
130                 135                 140

Ile Leu Tyr Lys Arg Glu Thr Thr His Ser Ala Ser Phe Cys Gly Ser
145                 150                 155                 160
```

```
Pro Tyr Ser Trp Glu Gln Glu Leu Gln His Gly Arg Leu Val Phe Gln
                165                 170                 175
Thr Ser Thr Arg His Gly Asp Glu Ser Phe Cys Ser Gln Ser Ser Gly
            180                 185                 190
Ile Leu Ser Arg Ser Ser Val Gly Pro Cys Val Arg Ser Gln Leu Lys
        195                 200                 205
Gln Ser Arg Leu Gly Leu Gln Pro Gln Gln Gly Ser Leu Ala Arg Gly
    210                 215                 220
Lys Ser Gly Arg Ser Gly Ser Ile Arg Ala Arg Val His Pro Thr Thr
225                 230                 235                 240
Arg Arg Ser Phe Gly Val Glu Pro Ser Gly Ser Gly His Ile Asp Asn
                245                 250                 255
Ser Ala Ser Ser Thr Ser Ser Cys Leu His Gln Ser Ala Val Arg Lys
            260                 265                 270
Thr Ala Tyr Ser His Leu Ser Thr Ser Lys Arg Gln Ser Ser Ser Ala
        275                 280                 285
His Ala Val Glu Leu His Thr Ile Pro Pro Ser Ser Ala Arg Pro Gln
    290                 295                 300
Ser Glu Gly Pro Ile Leu Ser Cys Trp Trp Leu Gln Phe Arg Asn Ser
305                 310                 315                 320
Lys Pro Cys Ser Asp Tyr Cys Leu Thr His Ile Val Asn Leu Leu Glu
                325                 330                 335
Asp Trp Gly Pro Cys Thr Glu His Gly Glu His Asn Ile Arg Ile Pro
            340                 345                 350
Arg Thr Pro Ala Arg Val Thr Gly Gly Val Phe Leu Val Asp Lys Asn
        355                 360                 365
Pro His Asn Thr Thr Glu Ser Arg Leu Val Val Asp Phe Ser Gln Phe
    370                 375                 380
Ser Arg Gly Ser Thr His Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                405                 410                 415
Leu Asp Ala Ser Ala Ala Phe Tyr His Ile Pro Leu His Pro Ala Ala
            420                 425                 430
Met Pro His Leu Leu Val Gly Ser Gly Leu Pro Arg Tyr Val Ala
        435                 440                 445
Arg Leu Ser Ser Thr Ser Arg Asn Ile Asn Tyr Lys His Gly Thr Met
    450                 455                 460
Gln Asp Leu His Asp Ser Cys Ser Arg Asn Leu Tyr Val Ser Leu Leu
465                 470                 475                 480
Leu Leu Tyr Lys Thr Phe Gly Gln Lys Leu His Leu Tyr Ser His Pro
                485                 490                 495
Ile Ile Leu Gly Phe Arg Lys Ile Pro Met Gly Val Gly Leu Ser Pro
            500                 505                 510
Phe Leu Leu Ala Gln Phe Thr Ser Thr Ile Cys Ser Val Val Arg Arg
        515                 520                 525
Ala Phe Pro His Cys Leu Ala Phe Ser Tyr Met Asp Asp Val Val Leu
    530                 535                 540
Gly Ala Lys Ser Val Gln His Leu Glu Ser Leu Tyr Thr Ser Ile Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu Asn Phe Met Gly Tyr Val Ile Gly Cys Trp
```

```
            580                 585                 590
Gly Thr Leu Pro Gln Glu His Ile Val Leu Lys Ile Lys Gln Cys Phe
            595                 600                 605

Arg Lys Leu Pro Val Asn Arg Pro Leu Asp Trp Lys Val Cys Gln Arg
        610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
                645                 650                 655

Thr Phe Ser Pro Thr Tyr Lys Ala Phe Leu Cys Lys Gln Tyr Leu Asn
            660                 665                 670

Leu Tyr Pro Val Ala Arg Gln Arg Ser Gly Leu Cys Gln Val Phe Ala
        675                 680                 685

Asp Ala Thr Pro Thr Gly Trp Gly Leu Ala Ile Gly His Arg Arg Met
    690                 695                 700

Arg Gly Thr Phe Ala Ala Pro Leu Pro Ile His Thr Ala Glu Leu Leu
705                 710                 715                 720

Ala Ala Cys Phe Ala Arg Ser Arg Ser Gly Ala Lys Leu Ile Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
        755                 760                 765

Val Pro Ser Ala Leu Asn Pro Ala Asp Asp Pro Ser Arg Gly Arg Leu
    770                 775                 780

Gly Leu Tyr Arg Pro Leu Leu His Leu Pro Phe Arg Pro Thr Thr Gly
785                 790                 795                 800

Arg Thr Ser Leu Tyr Ala Val Ser Pro Ser Val Pro Ser His Leu Pro
                805                 810                 815

Asp Arg Val His Phe Ala Ser Pro Leu His Val Ala Trp Arg Pro Pro
            820                 825                 830

<210> SEQ ID NO 4
<211> LENGTH: 5
<212> TYPE: PRT
<213> ORGANISM: Unknown
<220> FEATURE:
<223> OTHER INFORMATION: epitope(subtype adr)

<400> SEQUENCE: 4

Arg Phe Leu Trp Glu
 1               5

<210> SEQ ID NO 5
<211> LENGTH: 5
<212> TYPE: PRT
<213> ORGANISM: Artificial Sequence
<220> FEATURE:
<223> OTHER INFORMATION: epitope(subtype ayw)

<400> SEQUENCE: 5

Lys Phe Leu Trp Glu
 1               5

<210> SEQ ID NO 6
<211> LENGTH: 15
<212> TYPE: PRT
<213> ORGANISM: Unknown
<220> FEATURE:
```

```
<223> OTHER INFORMATION: epitope(subtype adr)

<400> SEQUENCE: 6

Phe Ala Arg Phe Leu Trp Glu Trp Ala Ser Val Arg Phe Ser Trp
1               5                   10                  15

<210> SEQ ID NO 7
<211> LENGTH: 15
<212> TYPE: PRT
<213> ORGANISM: Unknown
<220> FEATURE:
<223> OTHER INFORMATION: epitope(subtype ayw)

<400> SEQUENCE: 7

Phe Gly Lys Phe Leu Trp Glu Trp Ala Ser Ala Arg Phe Ser Trp
1               5                   10                  15
```

EPITOPE AND ITS USE OF HEPATITIS B VIRUS SURFACE ANTIGEN

CROSS REFERENCE TO RELATED APPLICATIONS

This application is a National Stage of International Application No. PCT/KR2011/005477 filed Jul. 25, 2011, claiming priority based on Korean Patent Application No. 10-2011-0064671 filed Jun. 30, 2011, the contents of all of which are incorporated herein by reference in their entirety.

TECHNICAL FIELD

The present invention relates to an epitope specific to Hepatitis B virus (hereinafter, referred to as 'HBV') and use thereof. Since the epitope disclosed herein is a conservative position on which modification due to mutation ('mutagenesis') does not occur, a composition including an antibody against the epitope or a vaccine composition including the epitope described above has very low possibility of causing degradation of curing efficacy by HBV mutation, thus being very useful for HBV treatment.

The present invention also relates to a method for production of an antigen specific antibody to the epitope described above and such antigen specific antibody to the epitope produced according to the present invention exhibits excellent specificity when administered in vivo.

BACKGROUND ART

HBV is a virus having DNA genomes belonging to Hepadnaviridae family and causes acute and/or chronic hepatitis. In general, HBV is classified into eight genotypes which have at least 8% different gene sequences to one another or, otherwise, divided into nine serotypes (i.e., adw, adr, ayw, ayr, or the like) on the basis of two antigenic determinants (that is, epitopes) (d/y, w/r) of HBV surface antigen (HBsAg). 350 million people worldwide have been infected with chronic HBV and, specifically, about 5 to 8% of the population in Korea and China has chronic HBV infection. HBV infection is a major cause of liver diseases and liver cancer in these regions. At present, although the above infection can be protected somewhat by the development of vaccines, lots of patients still suffer from chronic Hepatitis B infection caused by HBV. HBV-caused chronic infection may induce hepatitis as well as liver cirrhosis and liver cancer and, as compared to non-infected people, people with chronic infection show an increase in liver cancer about 300 times higher. According to WHO investigation, chronic hepatitis B is considered as a major cause of about 80% of liver cancers.

Chronic hepatitis B medicine recently developed as a nucleoside analogue and available on the market may include, for example, lamivudine, adefovir dipivoxil, etc. These medicines may interfere with a reverse transcriptase of HBV polymerase, in turn inhibiting HBV DNA replication. However, in the case where any one of the foregoing medicines is administered for a long term such as 3 years, about 75% of the patients have drug resistance viruses, thus entailing a problem of deterioration in the curing efficacy. In order to prevent vertical transmission or infection after liver transplantation, the foregoing medicines are commonly used with hepatitis B immunoglobulin (HBIG).

Currently HBIG is manufactured by ion-exchange purification and virus inactivation from plasma of donors with high anti-HBsAg antibody titer.

However, the currently available HBIG is not an ideal source of therapeutic antibody due to its limited availability, low specific activity and possible contamination of infectious agents.

It is known that antibodies generated in vivo by vaccines now used in the art are mostly antibodies recognizing 'a' epitope of HBV. However, mutants escaping such antibodies, for example, a G145R mutant generated by substituting glycine at 145 of the HBsAg with arginine has recently been reported. Additionally, a variety of escaping mutants have also been found, therefore, existing HBV medicines involve limitations in rendering satisfactory curing efficacy. Accordingly, there is an increasing demand for HBV treatment antibodies and/or HBV vaccines specifically bound to epitopes that correspond to sites necessary for the survival of HBV in association with HBV replication and does not cause mutation, thus not causing deterioration in curing efficacy due to mutation.

DISCLOSURE

Technical Problem

In order to solve the problems described above, the present invention provides HBV specific epitopes including RFLWE (SEQ ID NO: 4) or KFLWE (SEQ ID NO: 5) and, in particular, an epitope having an amino acid sequence such as FARFLWEWASVRFSW (SEQ ID NO: 6) or FGKFLWEWASARFSW (SEQ ID NO: 7) that is a necessary site for the survival of HBV, thus corresponding to a conservative position on which mutation does not occur.

Another object of the present invention is to provide methods for production of the epitope described above, a HBV vaccine composition or vaccine comprising the epitope and an antibody capable of specifically binding to the epitope by applying the foregoing epitope, as well as a HBV treatment composition or curing agent including the antibody produced as described above.

A still further object of the present invention is to provide a composition or kit for HBV detection having the epitope described above or a polynucleotide sequence encoding the epitope.

Technical Solution

The inventors of the present invention have found that; epitopes of a human antibody specifically binding to a HBV surface antigen (see PCT/KR2010/004445, hereinafter referred to as the 'inventive antibody') correspond to sequences including RFLWE (SEQ ID NO: 4) or KFLWE (SEQ ID NO: 5) and, in particular, sequences derived from FARFLWEWASVRFSE (SEQ ID NO: 6) or FGKFLWEWASARFSE (SEQ ID NO: 7) or a part thereof; and such epitope sites are favorably conservative, significant for HBV replication and necessary for HBV survival. Therefore, the present invention has been completed under the foregoing discovery. Among the afore-mentioned epitopes, the epitopes having SEQ ID NO. 4 and SEQ ID NO. 6 are epitopes of adr subtypes (SEQ ID NO: 1) of HBV while the epitopes having SEQ ID NO. 5 and SEQ ID NO. 7 correspond to epitopes of ayw subtypes (SEQ ID NO: 2) of HBV.

The HBV specific epitope defined by any one of SEQ ID NOS. 4 to 7 according to the present invention may retain a three-dimensional structure or may be used as a conjugated form with a carrier, in order to improve efficiency when used for a composition such as a vaccine. The carrier used herein may include any one, which is bio-available and renders desired effects of the present invention, and be selected from peptide, serum albumin, immunoglobulin, hemocyanin, polysaccharides, or the like, without being particularly limited thereto.

The HBV specific epitope defined by any one of SEQ ID NOS. 4 to 7 as such or a composite thereof combined with a carrier may be useable as a vaccine composition for HBV treatment. In this regard, the vaccine composition may further include a pharmaceutically acceptable adjuvant or excipient. Such an adjuvant serves to facilitate formation of an antibody by injecting in vivo the adjuvant, and may include any one enabling achievement of purposes of the present invention, more particularly, at least one selected from aluminum salts $(Al(OH)_3, ALPO_4)$, squalene, sorbitane, polysorbate 80, CpG, liposome, cholesterol, monophosphoryl lipid (MPL) A and glucopyranosyl lipid (GLA) A, without being particularly limited thereto.

A polynucleotide encoding the HBV specific epitope defined by SEQ ID NOS. 4 to 7 and provided according to the present invention may be used as DNA vaccine. Here, the polynucleotide may be used as such without any vector or, otherwise, supported in a viral or non-viral vector. The viral or non-viral vector used herein may include any one commonly available in the art (to which the present invention pertains). The viral vector preferably includes adenovirus, adeno-associated virus, lentivirus, letrovirus, etc., while the non-viral vector may include a cationic polymer, a non-ionic polymer, liposome, lipid, phospholipid, a hydrophilic polymer, a hydrophobic polymer and a combination of at least one selected from the foregoing materials, without being particularly limited thereto.

The present invention provides a recombinant vector including a polynucleotide that encodes the HBV specific epitope defined by any one of SEQ ID NOS. 4 to 7 according to the present invention, a host cell including the recombinant vector, and a method for production of the HBV specific epitope defined by any one of SEQ ID NOS. 4 to 7 according to the present invention, using the recombinant vector or host cell described above.

In the present invention, the 'recombinant vector' is an expression vector that represents a target protein from a suitable host cell which is a gene product containing a necessary regulating element operably linked to a gene insert to express the gene insert. In the present invention, the term 'operably linked' refers to a nucleic acid expression control sequence functionally linked to a nucleic acid sequence encoding the target protein, so as to execute general functions. The operable linkage with the recombinant vector may be performed by gene recombination technologies well known in the art to which the present invention pertains. Site-specific DNA cleavage and linkage may also be easily performed using enzymes commonly known in the art to which the present invention pertains.

Appropriate expression vectors useable in the present invention may include signal sequences for membrane targeting or secretion as well as expression control elements such as a promoter, a start codon, a stop codon, a polyadenylated signal, an enhancer, or the like. The start codon and stop codon are generally considered as a part of a nucleotide sequence encoding an immunogenic target protein and, when administering a gene product, must exhibit an action in an individual while being in-frame with a coding sequence. The general promoter may be structural or inductive. A prokaryotic cell may include, for example, lac, tac, T3 and T7 promoters, without being particularly limited thereto. An eukaryotic cell may include, for example, monkey virus 40 (SV40), a mouse breast tumor virus (MMTV) promoter, human immunity deficient virus (HIV) and, in particular, a long terminal repeat (LTR) promoter of HIV, Moloney virus, cytomegalovirus (CMV), Epstein bar virus (EBV), Rous sarcoma virus (RSV) promoter, as well as β-actin promoter, human hemoglobin, human muscle creatin, human metallothionein derived promoter, without being particularly limited thereto.

The expression vector may include a selection marker to select a host cell containing a vector. The selection marker functions to sort cells transformed into vectors and may include markers providing selectable phenotypes such as drug resistance, nutrient requirements, tolerance to cellular cytotoxicity, expression of surface protein, etc. Since cells expressing the selection marker under selective agent-treated conditions only are alive, transformed cells may be screened. For a replicable expression vector, the vector may have a replication origin as a particular nucleic acid sequence at which replication starts. The expressed recombinant vector may include a variety of vectors such as plasmid, virus, cosmid, etc. The recombinant vector is not particularly limited so long as various host cells of prokaryotes and eukaryotes express desired genes and produce desired proteins, however, is preferably a vector to produce a great quantity of foreign proteins similar to a natural one, which possess a promoter having strong activity while attaining strong expression.

In particular, in order to express HBV specific epitopes defined by any one of SEQ ID NOS. 4 to 7, a variety of expression host-vector combinations may be used. An expression vector suitable for eukaryote may include expression control sequences derived from; for example, SV40, bovine papilloma virus, adenovirus, adeno-associated virus, cytomegalovirus, lenti-virus and/or retro-virus, without being particularly limited thereto. The expression vector used for bacteria hosts may include, for example: bacterial plasmids obtained from *Escherichia coli* such as pET, pRSET, pBluescript, pGEX2T, pUC vector, col E1, pCR1, pBR322, pMB9, and derivatives thereof; plasmids such as RP4 with a wide range of hosts; phage DNA exemplified as various phage lambda derivatives such as λgt10 and λgt11, NM980, etc.; other DNA phages such as single-stranded filament type DNA phage, M13, or the like. A vector useful for insect cells may be pVL941.

The recombinant vector is inserted in a host cell to form a transformant and the host cell suitably used herein may include, for example: prokaryotes such as *E. coli, Bacillus subtilis, Streptomyces* sp., *Pseudomonas* sp., *Proteus mirabilis* or *Staphylococcus* sp.; fungi such as *Aspergillus* sp.; yeasts such as *Pichia pastoris, Saccharomyces cerevisiae, Schizosaccharomyces* sp., *Neurospora crassa*, etc.; eukaryotic cells such as lower eukaryotic cells, higher eukaryotic cells, i.e., insect cells, or the like. The host cell is preferably derived from plants and/or mammals and, in particular, derived from monkey kidney cells 7 (COST), NSO cells, SP2/O, Chinese hamster ovary (CHO) cells, W138, baby hamster kidney (BHK) cells, MDCK, myeloma cell lines, HuT 78 cells and/or HEK293 cells, without being particularly limited thereto. Most preferably, CHO cells are used.

In the present invention, the term 'transformation into host cells' includes any technique for introduction of nucleic acid into organics, cells, tissues and/or organs and, as well known in the conventional art, a standard technique may be suitably selected depending upon the host cells to perform the transformation. Among such techniques, electroporation, protoplasm fusion, calcium phosphate $(CaPO_4)$ precipitation, calcium chloride $(CaCl_2)$ precipitation, agitation using silicon carbide fibers, agro-bacteria mediated transformation, transformation mediated with PEG, dextrane sulfate and lipofectamine and through drying/inhibition, without being particularly limited thereto. By incubating a transformant in which the recombinant vector is expressed in a culture medium, the HBV specific epitope defined by any one of SEQ ID NOS. 4 to 7 may be formed in large quantities. The culture medium and culturing conditions may be suitably selected among those commonly used depending on host cells being used. During culturing, some conditions such as a temperature, pH of the medium, a culturing time, etc., may be controlled to enable appropriate cell growth and mass-production of proteins. As described above, the HBV specific epitope defined by any one of SEQ ID NOS. 4 to 7 may be collected from the medium or cell decomposition product by a recombination way and separated or purified by any conventional biochemical separation technique (Sambrook et al., Molecular Cloning: A Laboratory Manual, $2^{nd}$ Ed., Cold Spring Harbor Laboratory Press (1989); Deuscher, M., Guide to Protein Purification Methods Enzymology, Vol. 182. Academic Press, Inc., San Diego, Calif. (1990)). For this purpose, various methods such as electrophoresis, centrifugation, gel filtration, precipitation, dialysis, chromatography (ion-exchange chromatography, affinity chromatography, immuneadsorption chromatography, size exclusion chromatography, etc.), isoelectric point focusing, and various variations and combinations thereof may be utilized, without being particularly limited thereto.

The present invention provides a method for expressing the HBV specific epitope defined by any one of SEQ ID NOS. 4 to 7 on the surface of microorganisms or virus. In this case, a recombinant vector including a sequence that encodes an inducing promoter or a signal protein, as well as various microorganisms or viruses having the above recombinant vector may be used. More particularly, recombinant *E. coli*, yeast and/or bacteriophage are appropriate microorganisms and/or viruses, without being particularly limited thereto. In order to express the HBV specific epitope defined by any one of SEQ ID NOS. 4 to 7 on the surface of the foregoing microorganisms or viruses, display techniques well known in the art to which the present invention pertains may be used. Specifically, a polynucleotide sequence encoding the HBV specific epitope defined by any one of SEQ ID NOS. 4 to 7 may be combined with (or bound to) a sequence encoding a promoter or a signal protein that derives expression on the surface of a microorganism cell or virus, thus expressing the HBV specific epitope. Alternatively, after deleting a part of gene sites at which the surface expressing protein is encoded, a polynucleotide sequence encoding the HBV specific epitope defined by any one of SEQ ID NOS. 4 to 7 may be inserted into the deleted part. However, the present invention is not particularly limited to the foregoing methods. According to the afore-mentioned methods, the HBV specific epitope defined by any one of SEQ ID NOS. 4 to 7, which is expressed on the surface of the microorganism or virus, may be separated as such and purified for desired uses according to the present invention. In addition, the inventive epitope may be used to screen an antibody specifically bound to the HBV specific epitope defined by any one of SEQ ID NOS. 4 to 7, which is expressed on the surface, and then obtaining the screened antibody.

Furthermore, the present invention provides a method for production of an antibody specific bound to the HBV specific epitope defined by any one of SEQ ID NOS. 4 to 7, or fragments of the antibody, which includes using the HBV specific epitope defined by any one of SEQ ID NOS. 4 to 7, a composite containing the foregoing epitope or a polynucleotide encoding the foregoing epitope. Such antibody may be a polyclonal antibody or monoclonal antibody and, so long as fragments thereof have characteristics of being bound to the HBV specific epitope defined by any one of SEQ ID NOS. 4 to 7, they are also included within the scope of the present invention. More particularly, the inventive antibody or fragments thereof may include, for example: single-chain antibodies; diabodies; triabodies; tetrabodies; Fab fragments; F(ab')$_2$ fragments; Fd; scFv; domain antibodies; dual-specific antibodies; minibodies; scap; IgD antibodies; IgE antibodies; IgM antibodies; IgG1 antibodies; IgG2 antibodies; IgG3 antibodies; IgG4 antibodies; derivatives in antibody-unvariable regions; and synthetic antibodies based on protein scaffolds, all of which have the binding ability to the HBV specific epitope defined by any one of SEQ ID NOS. 4 to 7, without being particularly limited thereto. So long as characteristics of the inventive antibody are retained, antibodies mutated in variable regions may also be included within the scope of the present invention. This may be exemplified by conservative substitution of an amino acid in a variable region. Here, such 'conservative substitution' usually refers to substitution of an amino acid into another amino acid residue having similar properties to the original amino acid sequence. For example, lysine, arginine and histidine have base side-chains, in turn showing similar properties. On the other hand, both aspartic acid and glutamic acid have acid side-chains and exhibit similar properties to each other. In addition, glycine, asparagine, glutamine, serine, threonine, tyrosine, cysteine and tryptophan are similar to one another since they have non-charged polar side-chains, while alanine, valine, leucine, threonine, isoleucine, proline, phenylalanine and methionine are similar to one another since they have non-polar side-chains. Further, tyrosine, phenylalanine, tryptophan and histidine are similar to one another since they have aromatic side-chains. Consequently, it will be obvious to those skilled in the art that, even though amino acid substitution occurs within any one of the foregoing groups having similar properties, significant change in characteristics may not be found. Therefore, if specific properties of the inventive antibody are retained, a method for production of antibodies having mutated due to conservative substitution in a variable region may also be included within the scope of the present invention.

The antibody bound to the HBV specific epitope defined by any one of SEQ ID NOS. 4 to 7 may be prepared by any conventional method known in the art (to which the present invention pertains). More particularly, after inoculating an animal with the HBV specific epitope defined by any one of SEQ ID NOS. 4 to 7, a composite including the epitope or a polynucleotide encoding the epitope described above, an antibody specifically bound to the HBV specific epitope defined by any one of SEQ ID NOS. 4 to 7 is produced and screened from the inoculated animal, in turn being obtainable.

The animal used herein may include a transgenic animal, in particular, a transgenic mouse capable of producing the same antibody as a human-derived sequence. The so-called fully human antibody having decreased immunogenicity, which is obtained using a transgenic mouse, may be produced according to any one of the methods disclosed in: U.S. Pat. Nos. 5,569,825; 5,633,425; and 7,501,552, or the like. In the case where the afore-mentioned animal has not been preferably transformed to allow production of the same antibody as the human-derived sequence, a humanization or deimmunization process may be further implemented, using the antibody obtained from the animal, according to any one of the methods disclosed in: U.S. Pat. Nos. 5,225,539; 5,859,205; 6,632,927; 5,693,762; 6,054,297; 6,407,213; and WO Laid-Open Patent No. 1998/52976, thus suitably processing the antibody to be useful for in vivo treatment. More particularly, such humanization or deimmunization may include CDR-grafting to graft a CDR sequence of an antibody produced from an animal into a framework of a human antibody and, in order to increase affinity or decrease immunogenicity, further include a CDR-walking process to substitute, insert and delete at least one amino acid sequence.

Instead of the HBV specific epitope defined by any one of SEQ ID NOS. 4 to 7, a composite including the epitope and/or a polynucleotide encoding the epitope, if the overall HBV is used as an immunogen, a process of predominantly screening (often 'panning') antibodies having HBV binding ability (sometimes abbreviated to 'binding') and then additionally panning antibodies to specifically recognize the HBV specific epitope defined by any one of SEQ ID NOS. 4 to 7, among the primarily screened antibodies, may be used. Alternatively, a method for screening antibodies, which have no binding or decreased binding to HBVs mutated at important sites of the HBV specific epitope defined by any one of SEQ ID NOS. 4 to 7, among primarily screened HBV binding antibodies, wherein the method includes deriving mutation at the important sites of the HBV specific epitope defined by any one of SEQ ID NOS. 4 to 7, may also be used.

Meanwhile, according to display techniques well known in the art, human antibodies bound to the HBV specific epitope defined by any one of SEQ ID No. 4 to 7 may be produced and screened. Such display techniques may be selected from a phage display, a bacterial display or a ribosome display, without being particularly limited thereto. Production and display of libraries may be easily performed according to the conventional art disclosed in, for example; U.S. Pat. Nos. 5,733,743, 7,063,943, 6,172,197, 6,348,315, 6,589,741, or the like. Especially, the libraries used in the foregoing display may be designed to have the sequences of human-derived antibodies. More particularly, the method described above may be characterized by screening (or panning) antibodies specifically bound to the HBV specific epitope defined by any one of SEQ ID NOS. 4 to 7 only, by applying the HBV epitope defined by any one of SEQ ID NOS. 4 to 7 or a composite including the epitope.

Finally, the present invention provides a HBV detecting composition or kit, which includes the epitope defined by any one of SEQ ID NOS. 4 to 7, a composite including the epitope or a polynucleotide encoding the epitope. The HBV detecting composition or kit according to the present invention may have merits of enabling rapid and precise diagnosis of HBV infection while not under significant influence of HBV mutation. The HBV detection kit, which includes the epitope defined by any one of SEQ ID NOS. 4 to 7, a composite including the epitope or a polynucleotide encoding the epitope, may be fabricated to utilize a variety of methods including, for example, a general enzyme-linked immunosorbent assay (ELISA), a fluorescence-activated cell sorting (FACS) method, or the like. Moreover, in the case where the polynucleotide encoding the epitope of the present invention is used, hybridization may be detected by common hybridization techniques Advantageous Effects As is apparent from the detailed description, the HBV specific epitope provided according to the present invention is substantially a conservative position on which mutagenesis does not occur. Therefore, a composition or vaccine composition including an antibody against the foregoing epitope has relatively low possibility of causing deterioration in curing efficacy by such HBV mutation, thereby being effectively used in HBV treatment and/or diagnosis.

DESCRIPTION OF DRAWINGS

The above and other objects, features and advantages of the present invention will become apparent from the following description of preferred embodiments given in conjunction with the accompanying drawings, in which.

BEST MODE

Hereinafter, preferred embodiments of the present invention will be described in detail with reference to examples, however, such examples are for illustrative purposes only and not intended to limit the scope of the present invention.

Example 1

Identification of Epitope of Inventive Antibody

In order to identify the epitope of the inventive antibody, after causing random mutagenesis in the surface antigen protein of HBV adr subtypes (see SEQ ID NO. 1), binding of the inventive antibody to respective mutants was investigated. Here, preparation of the mutants and assay of the binding of the inventive antibody were implemented according to shotgun mutagenesis available from Integral Molecular Co. (J Am Chem Soc. 2009; 131(20): 6952-6954). Characteristics of mutation libraries used for identifying the epitope are shown in the following Table 1. After infecting HEK-293T cells with clones having the above libraries, the binding of the inventive antibody was assayed by immune-fluorescence assay.

The binding of the inventive antibody was determined by averaging results from tests repeated three times and subjected to normalization based on the binding of a wild type HBV surface antigen protein. In this case, using a rabbit polyclonal antibody against the HBV surface antigen protein, expression of the mutated surface antigen protein and the binding of the inventive antibody to such expression were investigated.

TABLE 1

Characteristics of library used for epitope identification

| | |
|---|---|
| Number of clones in library | 441 |
| Amino acid residues (AAs) of mutated HBV surface antigen | 223 (of total 226) |
| Average number of AA mutations per clone | 1.2 |
| Average number of mutations per AA residue | 2.4 |
| Number (percentage) of AAs mutated at least once | 223 (99%) |
| Number (percentage) of AAs mutated at least twice | 216 (96%) |
| Number (percentage) of clones containing a single AA mutation | 357 (81%) |
| Number (percentage) of clones containing two AA mutations | 76 (17%) |
| Number (percentage) of clones containing more than two AA mutations | 8 (2%) |

Figure 1:
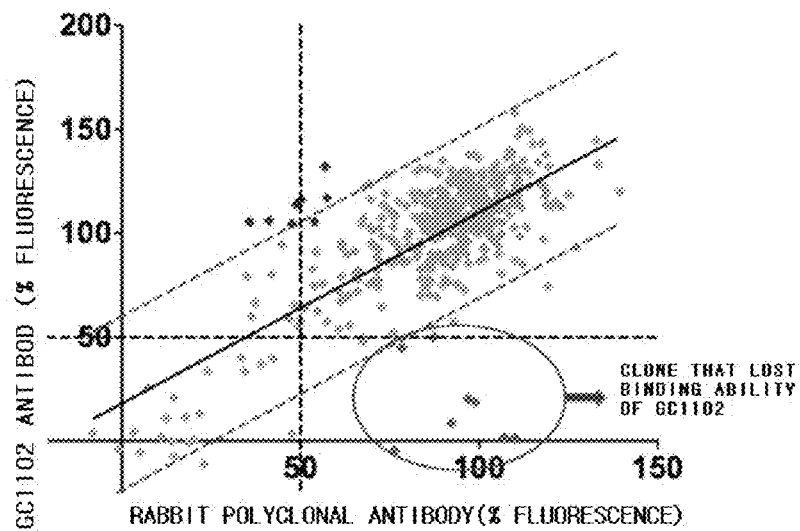
FIG. 1 illustrates analysis results of variation in binding ability to HBV surface antigen protein mutants in order to identify epitopes of the inventive antibody.

From the table, it was found that the inventive antibody lost the binding ability to eight (8) clones having mutation occurring at three amino acid residues (AAs) of the HBV surface antigen protein (see FIG. 1). That is, for the eight clones shown in FIG. 1, it was confirmed that the rabbit polyclonal antibody exhibited the binding ability, in turn normally expressing the mutated HBV surface antigen protein, however, the inventive antibody was not bound thereto.

As a result of assaying the eight clones, it was found that each has at least one mutation at 160R (160R means the amino acid R located at position 160, hereinafter the same as above), 163W and 164E (SEQ ID NO. 1), respectively. That is, the above sequence may be determined as a site corresponding to the epitope of the inventive antibody. From such result, it was found that the epitope of the inventive antibody contains RFLWE (SEQ ID NO. 4) and the epitope in ayw subtype of HBV with the binding ability contains KFLWE (SEQ ID NO. 5).

Figure 2:
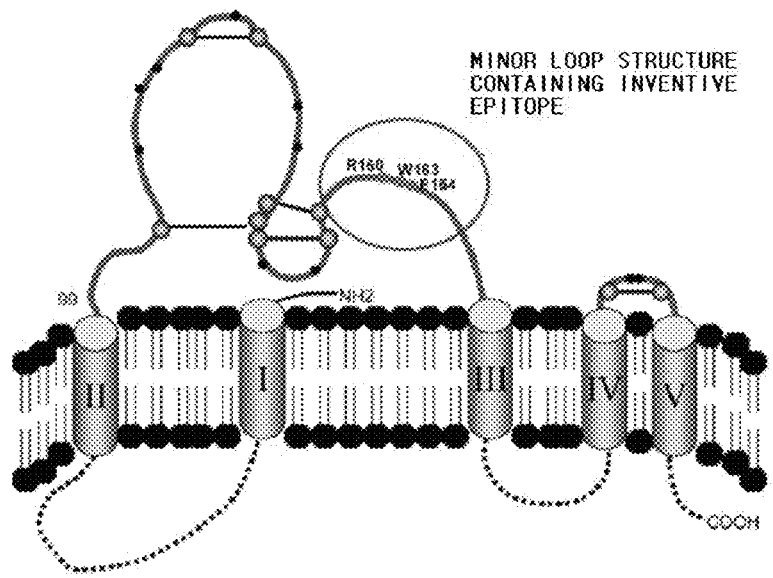
FIG. 2 shows a loop structure in HBV surface antigen protein including the inventive epitope.

Specifically, the epitope having the sequence defined by SEQ ID NOS. 4 or 5 may be FARFLWEWASVRFSW (SEQ ID NO. 6) or FGKFLWEWASARFSW (SEQ ID NO. 7) corresponding to a minor loop among two loops at HBV surface site at which the above epitope is present (see FIG. 2).

Example 2

Figure 3:
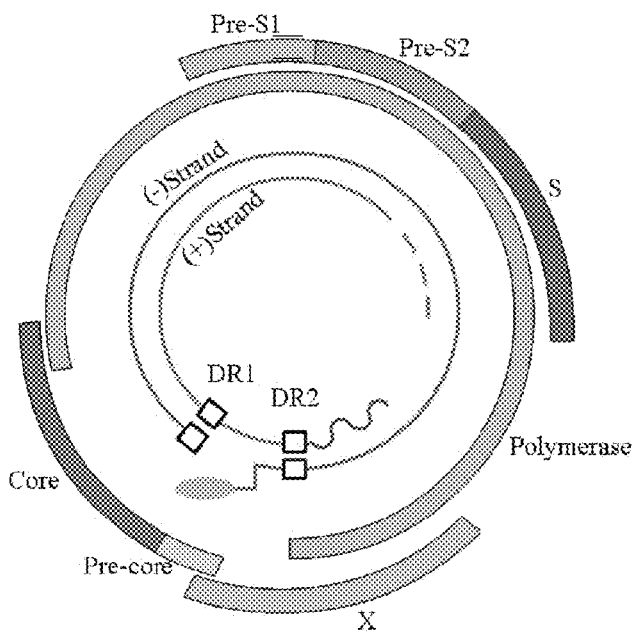
FIG. 3 illustrates a HBV genomic structure wherein the genome S ORF encoding the surface antigen protein is partially overlapped with the genome P ORF encoding a polymerase.

Identification of Characteristics of Epitope of Inventive Antibody (1) Preparation of HBV Polymerase (HBV Pol) Mutants Epitopes of the inventive antibody include 160K, 163W and 164E (SEQ ID NO. 2) in the surface antigen ORF (S ORF) of the HBV ayw subtype, wherein the ORF sequence of the HBV surface antigen encoding the epitopes overlaps with HBV P ORF encoding the HBV polymerase. In particular, 504I, 506M, 507G and 508V (see SEQ ID NO. 3) of the HBV polymerase may correspond to the sites at which the epitope is encoded by genes in the OFR encoding the epitope (see FIG. 3). Briefly, mutation at the foregoing sites in the HBV S ORF also involves mutation of the HBV P ORF.

The HBV polymerase has remarkably different features from other viral polymerases. First, the HBV polymerase has reverse transcriptase activity that synthesizes it's DNA from RNA (pregenomic RNA: pgRNA); second, during reverse transcription initiation, the HBV polymerase uses itself as the primer to conduct protein-priming; and third, primer translocation and template switching are executed during replication, although the correct mechanism is not still identified.

Meanwhile, as described above, an open reading frame ('ORF') that encodes the epitope site of the inventive antibody neutralizing HBV, that is, the epitope site of the inventive antibody in the HBV surface antigen, may overlap with another ORF encoding the HBV polymerase. Therefore, in order to survey influence by the HBV polymerase site, which is encoded by the HBV P ORF overlapping with the ORF encoding the epitope of the inventive antibody, upon HBV virus replication, mutation possibility of the foregoing epitope was investigated.

Figure 4:
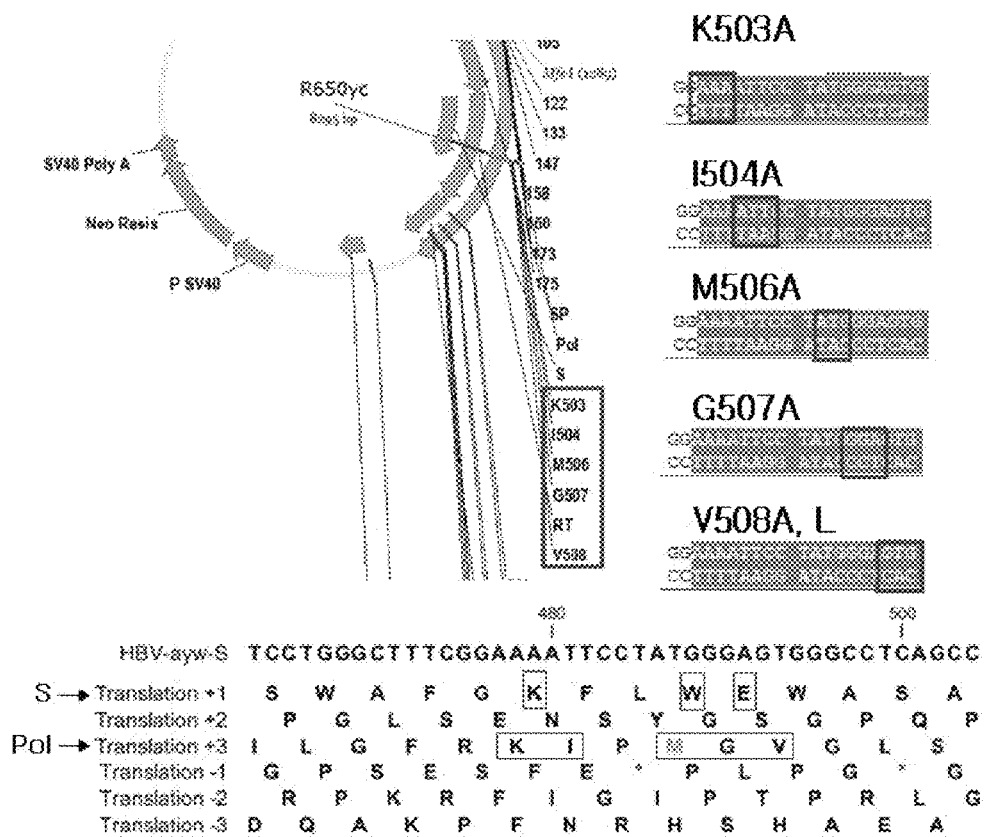
FIG. 4 illustrates a process of preparing mutants of the HBV polymerase.
Figure 5:
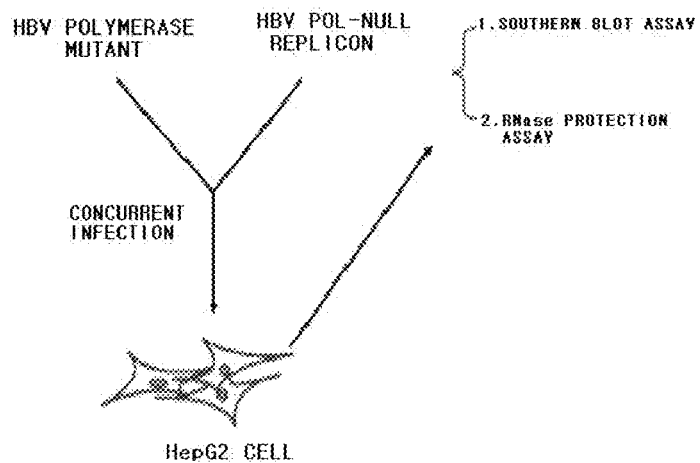
FIG. 5 illustrates a complementation test process executed by infecting HepG2 cell with a HBV Pol-free replicon and a HBV polymerase mutant, simultaneously.

For this purpose, a mutant substituting an amino acid, which is present at the site overlapping with the epitope of the inventive antibody in the HBV P ORF, into an alanine, was prepared through manipulation and subjected to survey of influence of the prepared mutant upon reverse transcriptase activity of a HBV polymerase ('HBV Pol'). First, the mutants such as K503A (K503A means that the amino acid K at the site 503 is mutated into A, hereinafter the same as above) I504A, M506A, G507A and V508A, which are obtained by substituting 503K, 504I, 506M, 507G and 508V of the HBV Pol polymerase with alanines, as well as a naturally generated mutant V508L have been prepared as shown in FIG. 4. Then, the variation in genome replicating function of the HBV polymerase having a mutant at the foregoing epitope site, has been investigated through complementation tests. In particular, HBV Pol-null replicon as a HBV mutant in which frame-shift mutation is derived in HBV P ORF and to which the HBV polymerase shows lack of activity, as well as a plasmid expressing the HBV polymerase in which mutation is derived as described above, have been infected HepG2 cells (see FIG. 5). Thereafter, HBV genome replication was assayed by Southern blot analysis and RNase protection assay (RPA).

(2) Southern Blot Analysis

As described above, the HBV Pol-null replicon and the mutant deriving mutation of the HBV polymerase have simultaneously infected HepG2 cell, followed by collection of replicated virus DNAs after 4 days. The collected materials were subjected to assessment of HBV DNA replication.

Figure 6:
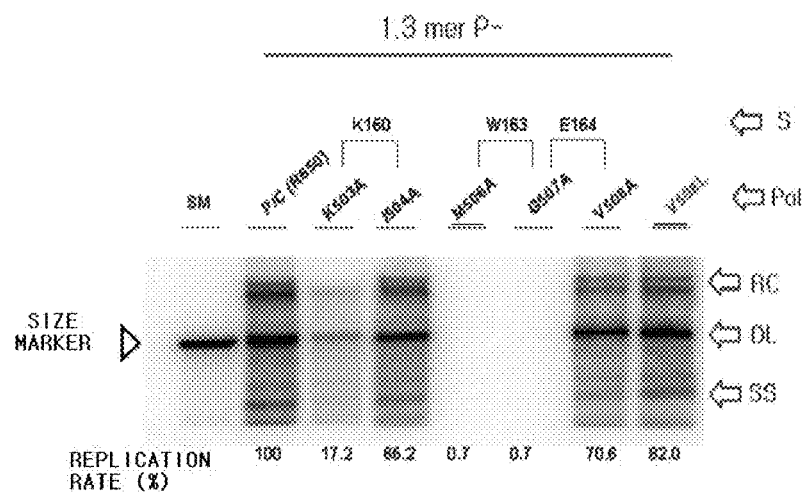
FIG. 6 shows test results of HBV replication ability of each HBV polymerase mutant through Southern blot analysis (comparison of HBV DNA replication intermediates, i.e., RC, DL, SS DNA at the right side of the graph)

As a result, for K503A mutant, virus DNA replication was about 17%, compared to wild type. This result indicates that 503K site in the HBV polymerase significantly participates in a mechanism of virus DNA replication. On the contrary, M506A and G507A mutants have rarely showed virus DNA replication. This fact demonstrates that 506M and 507G are essential sites for virus DNA replication mechanism of the HBV polymerase. I504A, V508A and V508L mutants exhibited respectively about 65%, 70% and 82% of virus DNA replication, compared to the wild type. That is, it was observed that these mutants have received virus DNA replication substantially similar to that of the wild type. Consequently, it was determined that the above mutants have relatively low participation in HBV DNA replication (see FIG. 6).

(3) Results of RPA (RNase Protection Assay)

As a pre-stage before DNA replication, encapsidation of RNA (pregenomic RNA: pgRNA) was assayed via a RPA method (see Kim et al., 2009, J. Virol. 83: 8032-8040).

As described above, the HBV Pol-null replicon and the mutant deriving mutation of the HBV polymerase have simultaneously infected HepG2 cell, followed by collection of cores of the virus and total pgRNAs in cells after 3 days. The collected materials were subjected to quantitative assay of pgRNA packaging extent wherein the pgRNA is used as a template for HBV DNA replication.

Figure 7:
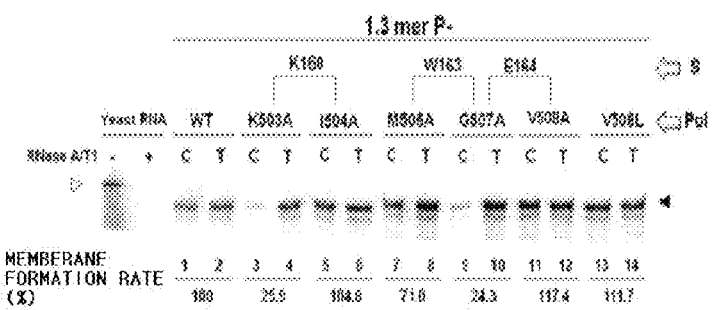
FIG. 7 shows test results of influences upon pregenomic RNA packaging by respective HBV polymerase mutants through RNase protection assay.

From the results, K503A and G507A mutants showed about 25% pgRNA packaging, compared to the wild type. This indicates that 503K and 507G significantly participate in packaging of the pgRNA into core particles of the virus. On the other hand, M506A mutant exhibited about 71% pgRNA packaging, compared to the wild type. That is, it was found that participation of 506M to pgRNA packaging is relatively low. Other mutants, i.e., I504A, V508A and V508L mutants showed pgRNA packaging substantially equal to the wild type, therefore, it is considered that these sites participate very little in pgRNA packaging (see FIG. 7).

(4) Overall Review for Influence of HBV Polymerase Mutants Upon HBV Replication

For K503A mutant of the HBV polymerase, only 25% pgRNA packaging resulted, compared to the wild type. As a result of quantifying the virus DNA as a final product of the virus replication, it was found that the replication was accomplished only to the extent of the pgRNA packaging. Accordingly, it is deemed that the 503K site mostly participates in the initial pgRNA packaging (see TABLE 2). On the other hand, M506A mutant of the HBA polymerase exhibited about 71% pgRNA packaging, which is substantially similar to that of the wild type. However, quantification results of virus DNAs as a final product of the virus replication revealed no replication. This fact means that, although M506 of the HBV polymerase never participates in pgRNA packaging, the M506 may significantly participate in a mechanism of virus DNA replication to synthesize (−)-strand DNAs using pgRNA as a template, i.e., a reverse transcription mechanism such as protein priming or primer translocation.

For G507A mutants of the HBV polymerase, pgRNA packaging was only 24% of the wild type and the virus DNA replication was executed very little and, therefore, it may be considered that M507 site has important functions in both the pgRNA binding and the reverse transcription of the polymerase. Further, the M507 site may have a role in interaction with a protein such as Hsp90 as a host factor and/or a core protein of the HBV, during encapsidation.

Meanwhile, the remaining mutants I504A, V508A and V508L of the HBV polymerase show pgRNA packaging and/or virus DNA replication substantially similar to those of the wild type. Accordingly, among sequences of the HBV polymerase that is encoded by HBV P ORF overlapping with HBV S ORF which encodes HBV surface antigen protein sites 160K, 163W and 164E found as the epitope of the inventive antibody, 160K and 163W sites are in close association with the virus replication. In the case where mutation is derived at these sites, virus replication may not be executed, thus being high conservative positions. Accordingly, the above two mutants do not exist and a specific-bound antibody to the foregoing sites may be effective in treating naturally generated mutants and/or mutants exhibiting tolerance by anti-viral medicines.

TABLE 2

Replication ability and RNA packaging characteristics of HBV polymerase mutants

| | Mutant | RNA packaging* | DNA replication* |
|---|---|---|---|
| HBV polymerase | K503A | + | + |
| | I504A | +++ | ++ |
| | M506A | ++ | − |
| | G607A | + | − |
| | V509A | +++ | ++ |
| | V508L | +++ | +++ |

*Compared to the wild type, +++: 70 to 100%; ++: 30 to 70%; +: 10 to 30%; and −: <1%

Example 3

Binding and Neutralization Effects of Inventive Antibody to Epitope Mutants (1) Preparation of Mutants At least one of 163W and 164E (SEQ ID NO. 1) of the HBV surface antigen protein (HBsAg), which are epitopes of the inventive antibody, was substituted by alanine, preparing a mutant. Since 160K relevant to serotypes has a problem in mutation, mutants thereof were excluded. In addition, mutants obtained by mutation of 164E into 164D have recently been reported, therefore, mutants of E164D were also prepared and used. Since the mutants were obtained as described above, mutation was also derived at 506M, 507G and 508V (SEQ ID NO. 2) of the HBV polymerase encoded by HBV P ORF overlapping with HBV S ORF which encodes the foregoing mutants. Here, even when the same amino acid mutation occurs depending upon variant codons at 163W and 164E of the HBV surface antigen protein, mutants of the HBV polymerase have different amino acid sequences (see TABLE 3).

TABLE 3

Mutants of HBsAg and Mutation of Corresponding HBV Polymerase

| Mutant | HBsAg mutation before | HBsAg mutation after | Mutation of HBV polymerase before | Mutation of HBV polymerase After |
|---|---|---|---|---|
| M5-1 | WE | AA | MGV | SRL |
| M5-2 | | AA | | SRV |
| M5-3 | | AA | | SGL |
| M5-4 | | AA | | SGV |
| M5-5 | | AE | | SRV |
| M5-6 | | AE | | SGV |
| M5-7 | | WA | | MGL |
| M5-8 | | WA | | MGM |
| M5-9 | | WA | | MGV |
| M6-1 | | WD | | MGL |

(2) Test and Validation of In Vivo Efficacy Using Acute Hepatitis B Derived Mouse By injecting HBV DNA into a C57BL6 mouse through hydrodynamic injection to derive symptoms similar to acute hepatitis B, the treated mouse was used to investigate binding of the inventive antibody, binding of HBV and/or HBV neutralization ability in the blood of the mouse where epitope mutation was derived as described above. The used C57BL6 mouse was a 6-week aged female with about a weight of 20 g, which is purchased from Charles Liver Laboratory (the United States). As shown in TABLE 4, a total of 12 groups with five mice per group were tested.

TABLE 4

Test conditions using C57BL6 mouse

| Subject | Number of Individuals | Test material and administering route | Dose |
|---|---|---|---|
| Wild type HBV | 5 | PBS, IV | 0.2 mL |
| Wild type HBV | 5 | 0.1 mg of inventive antibody, IV | 0.2 mL |
| M5-1 | 5 | 0.1 mg of inventive antibody, IV | 0.2 mL |
| M5-2 | 5 | 0.1 mg of inventive antibody, IV | 0.2 mL |

TABLE 4-continued

Test conditions using C57BL6 mouse

| Subject | Number of Individuals | Test material and administering route | Dose |
|---------|----------------------|---------------------------------------|------|
| M5-3 | 5 | 0.1 mg of inventive antibody, IV | 0.2 mL |
| M5-4 | 5 | 0.1 mg of inventive antibody, IV | 0.2 mL |
| M5-5 | 5 | 0.1 mg of inventive antibody, IV | 0.2 mL |
| M5-6 | 5 | 0.1 mg of inventive antibody, IV | 0.2 mL |
| M5-7 | 5 | 0.1 mg of inventive antibody, IV | 0.2 mL |
| M5-8 | 5 | 0.1 mg of inventive antibody, IV | 0.2 mL |
| M5-9 | 5 | 0.1 mg of inventive antibody, IV | 0.2 mL |
| M6-1 | 5 | 0.1 mg of inventive antibody, IV | 0.2 mL |

Figure 8:
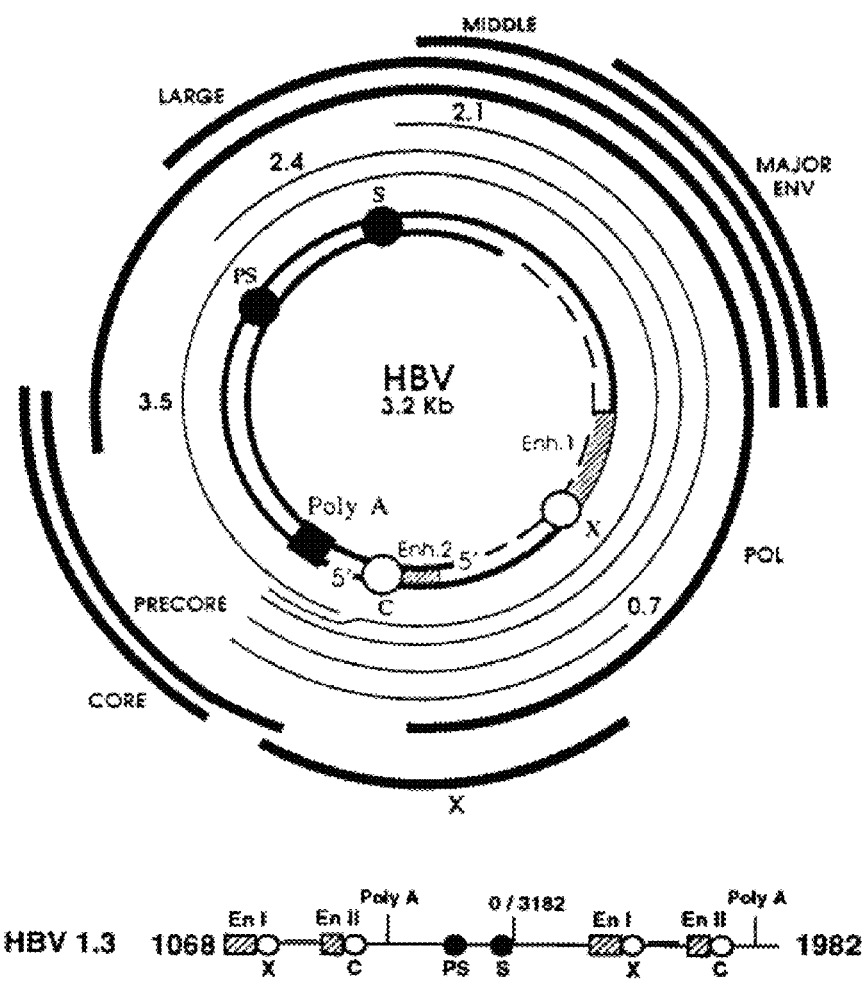
FIG. 8 shows a linkage map of HBV gene vector used in hydrodynamic injection in order to generate HBV virus particles in a mouse.

Each mouse was treated by injecting 20 μg of pHBV-MBRI vector (Shin et al., Virus Research 119, 146-153, 2006; see FIG. 8) that contains HBV DNA sequence inserted in pcDNA3.1 (Invitrogen, the United States) through a tail vein of the mouse at 0.3 mL/min with a ratio of 9.5% by volume per weight of the mouse, thus causing acute hepatitis B. After hours, as shown in TABLE 4, 0.2 mL of the inventive antibody was intravenously (IV) administered through the tail vein of the mouse. Before injection of the inventive antibody (24 hours, 48 hours) and after injection thereof (72 hours, 96 hours), the serum was separated and diluted to 10 times in a goat serum, followed by measuring a concentration in the blood of the HBV surface antigen protein (HBsAg) through Genedia HBsAg ELISA 3.0 (Green Cross Corp. MS, Korea). With regard to HBV DNA, before (48 hours) and after (72 hours) the injection of the inventive antibody, the blood was separated and analyzed by real time PCR to perform quantitative assay of HBV DNA in blood, and then, comparative assay of HBV neutralization ability of the inventive antibody.

As a result of detecting HBsAg in blood via Genedia HBsAg ELISA 3.0, it was confirmed that, if 10 mutants are inserted, all HBsAgs are suitably expressed. When 10 variant type HBsAgs were assayed on binding to the inventive antibody, the variant HBsAg in which both 163W and 164E were substituted with alanine, did not show binding to the inventive antibody. On the other hand, it was found that the variant HBsAg in which 163W only was substituted with alanine, shows the binding ability of 70% or higher, compared to the wild type. In addition, the variant HBsAg having 164E substituted with alanine exhibited the binding ability of about 30%, compared to the wild type. For E164D variant, binding characteristics were substantially similar to the wild type (see TABLE 5).

Mutation in HBsAg influences the sequences of the HBV polymerase as described above. Therefore, influences of a polymerase variant, which may be created by substitution of amino acid residues of HBsAg with alanines, upon HBV DNA replication, were assayed. The assayed results revealed that no HBV DNA replication occurs if 163W and 164E are all mutated. In particular, as a result of studying HBV DNA replication when both the 163W and 164E were respectively substituted with alanine, the 164E variant had HBV DNA replication of about 30 to 70% while the 163W variant showed no replication. Therefore, it was identified that amino acid sites in the polymerase corresponding to 163W site are very important for replication.

164E variants with HBsAg expression and HBV DNA replication were assayed to identify HBV neutralization ability of the inventive antibody. From results thereof, it was confirmed that the HBV neutralization ability is considerably decreased because the inventive antibody has a binding ability reduced to about 70%, compared to the wild type. However, for the 164D variant as a natural variant known in the art, the inventive antibody exhibited similar binding ability as the wild type.

TABLE 5

Neutralization efficacy of inventive antibody in relation to HBsAg mutation and influence thereof upon HBV DNA replication

| Mutant | HBsAg mutation Before | HBsAg mutation After | Polymerase mutation Before | Polymerase mutation After | Inventive antibody plate | Genedia plate | HBV DNA replication | Neutralization efficacy |
|--------|-----------------------|----------------------|----------------------------|---------------------------|--------------------------|---------------|---------------------|-------------------------|
| M5-1 | WE | AA | MGV | SRL | − | Binding | − | ND |
| M5-2 | | AA | | SRV | − | Binding | − | ND |
| M5-3 | | AA | | SGL | − | Binding | − | ND |
| M5-4 | | AA | | SGV | − | Binding | − | ND |
| M5-5 | | AA | | SRV | +++ | Binding | − | ND |
| M5-6 | | AE | | SGV | ++ | Binding | − | ND |
| M5-7 | | WA | | MGL | + | Binding | ++ | None |
| M5-8 | | WA | | MGM | + | Binding | + | None |
| M5-9 | | WA | | MGV | + | Binding | ++ | None |
| M6-1 | | WD | | MGL | +++ | Binding | +++ | Yes |

(*) Compared to the wild type, +++: 70 to 100%; ++: 30 to 70%; +: 10 to 30%; and −: <1%
ND: Verification test of neutralization ability was not implemented (Not Determined)

As described in the foregoing description, epitopes of the inventive antibody in HBsAg include 160K (ayw) or 160R (adr), 163W and 164E. More particularly, the site 164E was identified as the most influential position for binding the inventive antibody, through experiments using alanine substitution variants. At present, this position is known to be mutated into 164D and the inventive antibody also showed neutralization ability to the 164D variant. On the other hand, although the site 163W does not significantly participate in binding of the inventive antibody, mutation at this site causes mutation of the polymerase sequence that importantly serves to replicate, which in turn influences HBV DNA replication. Therefore, it may be predicted that the foregoing site is a highly conservative position, that is, a position at which mutation occurs very little. In fact, any mutation at 163W has not yet been reported. Lastly, 160K (for ayw subtype) or 160R (for adr subtype) are amino acid sites to determine serotypes. From results of functional assay, these were identified to be in close association with HBV replication, thus being predicted as highly conservative positions at which mutation occurs very little.

The invention claimed is:

1. A peptide consisting of the amino acid sequence of SEQ ID NO: 4, SEQ ID NO: 5, SEQ ID NO: 6, or SEQ ID NO: 7, said peptide being conjugated to a carrier, wherein the carrier is selected from the group consisting of serum albumin, immunoglobulin, hemocyanin and polysaccharide.

2. A vaccine composition comprising:
(a) at least one selected from the group consisting of a peptide of SEQ ID NO: 4 conjugated to a carrier, a peptide of SEQ ID NO: 5 conjugated to a carrier, a peptide of SEQ ID NO: 6 conjugated to a carrier, a peptide of SEQ ID NO: 7 conjugated to a carrier, and
(b) a pharmaceutically acceptable adjuvant to facilitate a formation of an antibody specifically binding to (a) when injected in vivo,
wherein the carrier is selected from the group consisting of serum albumin, immunoglobulin, hemocyanin and polysaccharide.

3. The vaccine composition of claim 2, wherein the adjuvant is at least one selected from the group consisting of aluminum salts, squalene, sorbitane, polysorbate 80, CpG, liposome, cholesterol, monophosphoryl lipid A and glucopyranosyl lipid A.

4. A method for production of an antibody or an antigen binding fragment thereof, in a host, which specifically binds to a Hepatitis B virus, comprising:
administering to the host any one selected from the group consisting of the following (i)-(iv):
(i) a peptide of SEQ ID NO: 4 conjugated to a carrier
(ii) a peptide of SEQ ID NO: 5 conjugated to a carrier,
(iii) a peptide of SEQ ID NO: 6 conjugated to a carrier, and
(iv) a peptide of SEQ ID NO: 7 conjugated to a carrier; and
isolating an antibody which binds to at least one of (i)-(iv) or an antigen-binding fragment of the antibody, produced in the host,
wherein the carrier is selected from the group consisting of serum albumin, immunoglobulin, hemocyanin and polysaccharide.

5. The method of claim 4, wherein the antibody is a polyclonal antibody or a monoclonal antibody.

6. The method of claim 4, further comprising subjecting the antibody or the antigen-binding fragment thereof to a humanization or deimmunization process.

7. The method of claim 6, wherein the humanization process includes grafting of complementarity determining region sequence of the antibody produced from an animal to framework region of a human antibody.

8. The method of claim 7, further comprising a process of substituting, inserting or deleting at least one amino acid sequence, in order to increase affinity or decrease immunogenicity.

9. The method of claim 4, wherein the host is a transgenic animal enabling production of the same antibody as a human-derived sequence.

10. The method of claim 9, wherein the transgenic animal is a transgenic mouse.

11. A composition for detecting hepatitis B virus, comprising the conjugated peptide of claim 1.

12. A hepatitis B virus (HBV) detection kit, capable of detecting an epitope of the HBV, the kit comprising the conjugated peptide of claim 1.

13. A method for detecting an anti-hepatitis B virus (HBV) antibody in a subject, comprising:
contacting a sample of the subject with any one of the following (i)-(iv):
(i) a peptide of SEQ ID NO: 4 conjugated to a carrier,
(ii) a peptide of SEQ ID NO: 5 conjugated to a carrier,
(iii) a peptide of SEQ ID NO: 6 conjugated to a carrier,
(iv) a peptide of SEQ ID NO: 7 conjugated to a carrier, and
detecting binding of an anti-HBV antibody with one of (i)-(iv),
wherein the carrier is selected from the group consisting of serum albumin, immunoglobulin, hemocyanin and polysaccharide.

\* \* \* \* \*